United States Patent
Greenwood

[19]

[11] Patent Number: 6,082,180
[45] Date of Patent: *Jul. 4, 2000

[54] ULTRASONIC FLUID DENSITOMETER FOR PROCESS CONTROL

[75] Inventor: Margaret S. Greenwood, Richland, Wash.

[73] Assignee: Battelle Memorial Institute, Richland, Wash.

[ * ] Notice: This patent is subject to a terminal disclaimer.

[21] Appl. No.: 09/178,030

[22] Filed: Oct. 21, 1998

[51] Int. Cl.$^7$ ...................................................... G01N 9/24
[52] U.S. Cl. .............................................................. 73/32 A
[58] Field of Search ................................ 73/32 A, 30.01, 73/30.04, 54.41, 64.53

[56] References Cited

U.S. PATENT DOCUMENTS

| | | | |
|---|---|---|---|
| 4,149,139 | 4/1979 | Kronk | 367/93 |
| 4,320,659 | 3/1982 | Lynnworth et al. | 73/589 |
| 4,571,693 | 2/1986 | Birchak et al. | 73/589 |
| 4,821,838 | 4/1989 | Chen | 181/175 |
| 4,893,496 | 1/1990 | Bau et al. | 73/32 A |
| 4,991,124 | 2/1991 | Kline | 73/32 A |
| 5,271,267 | 12/1993 | Baumoel | 73/32 A |
| 5,365,778 | 11/1994 | Sheen et al. | 73/54.41 |
| 5,708,191 | 1/1998 | Greenwood et al. | 73/32 A |

OTHER PUBLICATIONS

"Noninvasive Sensor Measures Fluid Density and Viscosity," *Sensors*, Oct., 1994, pp. 13–15.

Sheen et al., "An In–Line Ultrasonic Viscometer," *Review of Progress in Quantitative Nondestructive Evaluation*, vol. 14a pp. 1151–1158, 1995.

*Primary Examiner*—John E. Chapman
*Attorney, Agent, or Firm*—Paul W. Zimmerman

[57] ABSTRACT

The present invention is an ultrasonic fluid densitometer that uses at least one pair of transducers for transmitting and receiving ultrasonic signals internally reflected within a material wedge. A temperature sensor is provided to monitor the temperature of the wedge material. Density of a fluid is determined by immersing the wedge into the fluid and measuring reflection of ultrasound at the wedge-fluid interface and comparing a transducer voltage and wedge material temperature to a tabulation as a function of density.

6 Claims, 3 Drawing Sheets

6,082,180

ULTRASONIC FLUID DENSITOMETER FOR PROCESS CONTROL

This invention was made with Government support under Contract DE-AC06-76RLO 1830 awarded by the U.S. Department of Energy. The Government has certain rights in the invention.

FIELD OF THE INVENTION

The present invention is an apparatus and method for measuring fluid density. More specifically, the invention relies upon one or more acoustic transducers in combination with a temperature sensor mounted on or attached to a wedge material wherein the wedge material is immersed into the fluid for determination of the density of the fluid for process control of a fluid density.

BACKGROUND OF THE INVENTION

Use of sound waves, specifically ultrasonic sound waves for determining fluid density is well known. An ultrasonic sensor for measuring fluid density was reported by S. Sheen at Argonne National Laboratory. It received a R&D 102 Award in 1994 and a description appeared in the Research and Development magazine in October, 1994, p. 15.

Sheen describes an ultrasonic densitometer (FIG. 1) for measuring a density of a fluid 100. The ultrasonic densitometer has a wedge material 102 wherein the wedge material 102 has at least two sides substantially parallel. A first parallel side 104 has a first ultrasonic transducer 106 mounted thereon and a second parallel side 108 immersible into said fluid whereby a first portion of an ultrasonic signal emanating from said first ultrasonic transducer 106 strikes the second parallel side 108 and reflects back to the first parallel side 104 providing a reflection coefficient. A second portion of the ultrasonic signal propagates through the fluid 100, strikes a second wedge immersed surface 110 and reflects back to the first ultrasonic transducer 106 providing a speed of sound in the fluid. The arm surfaces 112 of the T are in contact with air for reference measurements. The T-shaped wedges 102 are mounted through the wall of a pipe 114 so that the fluid 100 within the pipe passes between the immersed surfaces 108, 110 of the two T-shaped wedges 102, 102a. From the reflection coefficient and the speed of sound in the fluid, the density of the fluid is obtained. In a second paper S. H. Sheen, H. T. Chien, and A. C. Raptis, "An In-Line Ultrasonic Viscometer," Review of Progress in Quantitative Nondestructive Evaluation, Vol. 14a, pp 1151–1158, 1995, Sheen specifies that the T-shaped wedge material is aluminum. The second transducer generates shear waves used for determining viscosity. A disadvantage of Sheen's ultrasonic densitometer is that because the wedge material is aluminum, the acoustic impedance of the wedge material is much greater than the acoustic impedance of the fluid so that a substantial change in density (eg. 10%) results in a quite small change in the aluminum/liquid reflection coefficient of about 0.014. Secondarily, the ultrasonic signal is required to reflect through the fluid of interest thereby requiring the requisite target surface of a second T-shaped wedge. Further, for fluids attenuative of ultrasound, density measurements would not be obtainable.

Another ultrasonic fluid meter is described in M. S. Greenwood, J. L. Mai, and M. S. Good, "Attenuation measurement of ultrasound in a kaolin-water slurry: A linear dependence upon frequency," A J. Acoust. Soc. Am. 94, 908–916 (1993). This ultrasonic attenuation sensor was developed for concentration measurements in a $\frac{1}{12}$-scale model of a double-shell tank. Because fluid density is a function of concentration, this unit may be used to determine fluid density as well as fluid concentration. The sensor consists of a send transducer and a receive transducer, separated by 4 inches. The ultrasound produced by the send transducer travels through a liquid (or slurry) where it is attenuated. The signal recorded by the receive transducer indicates how much attenuation has occurred. However, the instrument required calibration by making measurements in the laboratory for that specific slurry formulation so that concentration of the slurry could be correlated with voltage of signal in receive transducer. Again, this ultrasonic densitometer required that the ultrasonic signal be detected after passing through the fluid, in this case slurry, of interest and further required prior laboratory calibration.

Commercially available ultrasonic fluid concentration measuring devices are available through JM Science Inc, Buffalo, N.Y., Manufactured by: Fuji Ultrasonic Engineering Co., Ltd. In operation, an ultrasonic transducer produces ultrasound that propagates through the fluid of interest then is reflected by a metal plate about an inch away from the transducer. The reflected signal returns to the transducer and the time for a round trip is determined. Since the distance is known, the velocity of ultrasound in the liquid can be determined. The Fuji sensor correlates the speed of sound with a concentration of a particular fluid solution and with temperature of the particular fluid solution and requires laboratory calibration. As with Greenwood et al., the reflected ultrasonic signal must pass through the fluid of interest and the instrument requires calibration.

There is a need in the field of ultrasonic densitometry for an ultrasonic fluid densitometer that has greater sensitivity, does not require calibration and does not require a reflected signal to pass through the fluid of interest.

SUMMARY OF THE INVENTION

The present invention is an ultrasonic fluid densitometer that uses one or more ultrasonic transducers in combination with a temperature sensor on a material wedge. Density of a fluid is determined by immersing the wedge into the fluid and measuring reflection of ultrasound at the wedge-fluid interface.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

Figure 1:
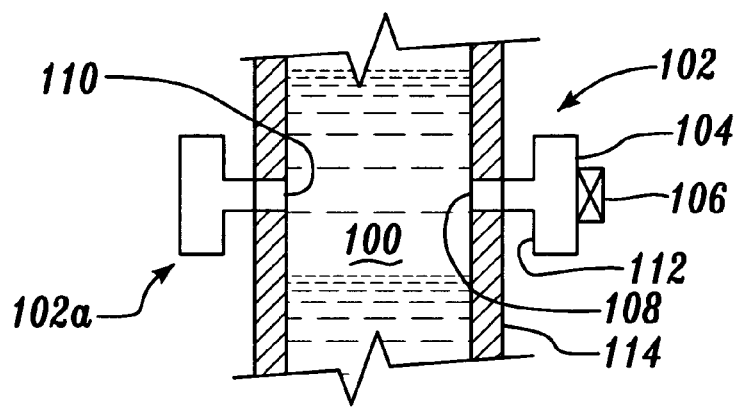
FIG. 1 is a cross section of a prior art ultrasonic densitometer.

The improvement, according to the present invention is that the combination of one or more transducers 106 with a temperature sensor 107 permits simple effective process control of fluid density. In a preferred embodiment, the wedge material 102 has a ratio of an acoustic impedance of the wedge material to an acoustic impedance of the fluid that is less than 11. Table 1 shows acoustic impedances for candidate wedge materials and ratio of acoustic impedance of those materials to the acoustic impedance of water which has an acoustic impedance of 1.5 ($10^6$) kg/m²s. By using a wedge material 102 having an acoustic impedance ratio to the fluid of less than 11, there is an increased change in reflection coefficient which increases the sensitivity of the ultrasonic densitometer. Specifically for Rexolite (C-LEC Plastics, Inc. Beverly, N.J.), for a 10% change in fluid density, there is a change of about 0.05 of the reflection coefficient.

TABLE 1

Acoustic Impedances

| Material | Acoustic Impedance (kg/m²s) | Ratio to Water |
|---|---|---|
| Aluminum | 17($10^6$) | 11.33 |
| Lead | 25($10^6$) | 16.67 |
| Steel | 45($10^6$) | 30.00 |
| Rexolite | 2.5($10^6$) | 1.67 |

It is preferred that the acoustic impedance ratio be less than about 5 and more preferably less than about 3 when the fluid is a liquid. Plastic includes polymers including but not limited to Rexolite, Loten (Sigma Transducers, Kennewick, Wash.), and acrylics. It is further preferred that the reflection coefficient transition from positive to negative with a zero value in between. Rexolite demonstrates this behavior with positive reflection coefficient above 38° angle of internal reflection and negative reflection coefficient below 38°, where 38° is known as a zero reflection coefficient angle. It is even further preferred that such an angle of internal reflection is within 5° of this zero reflection coefficient angle. In contrast, some other wedge materials (including other plastics and metals) have a negative value of the reflection coefficient for all angles when the base is immersed in liquids. A transducer pair may be mounted forming an angle with the fluid interface at any angle with respect to the perpendicular to the wedge base. However, the determination of the density is more accurate for a larger difference in angle between the two transducer pairs. For example, the two transducer pairs might have angles of 5° and 60°. Accordingly, in a preferred embodiment, at least one pair of transducer is mounted with five to ten degrees of the perpendicular to the wedge base.

In a preferred embodiment, at least two temperature sensors 107 are used, one on the liquid contact surface and one on an upper surface of the wedge material to confirm temperature uniformity of the wedge material.

Fluids that can be measured are preferably liquid. A liquid may be a liquid solution, or mixture having solid particles or immiscible phases. Immiscible phases include liquids and gases. In mixtures, it is preferred that the non-soluble phase be of a size smaller than a wavelength of the ultrasonic waves. It is further preferable that the mixture be homogenous and may require mixing. When a gas (eg air) phase is present, it is preferred to use a minimum measurement in a series of measurements to obtain the most accurate measure of density. The reason is that gas bubbles may adhere to the surface of the immersed wedge material and increase the reflectance of ultrasound at the wedge material-gas interface.

Figure 2:
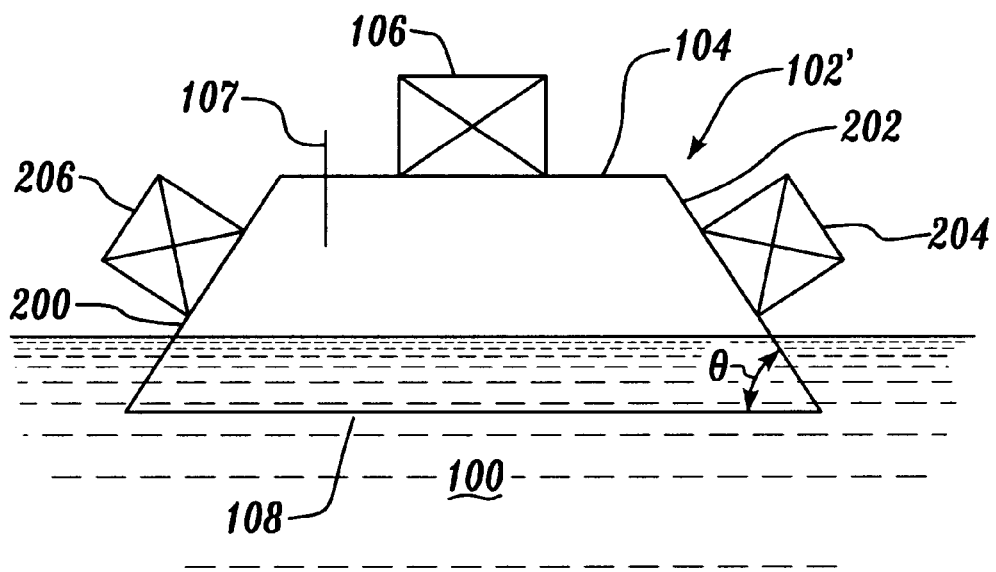
FIG. 2 is a three transducer embodiment of the present invention.
Figure 3:
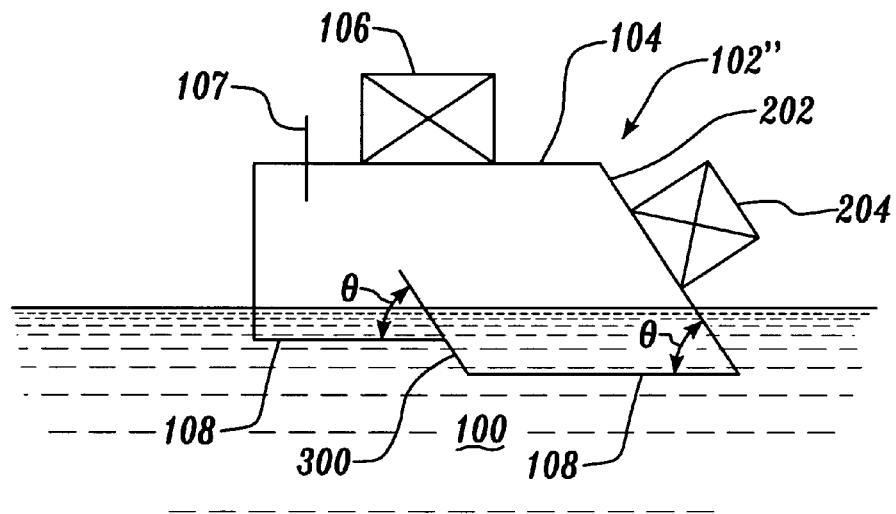
FIG. 3 is a two transducer embodiment of the present invention.

A further advantage is realized when all detected ultrasonic signals are detected on the basis of ultrasonic reflections internal to the wedge material as shown in FIGS. 2, 3, 4, and 5a. In FIGS. 2 and 3, the wedge material 102' and 102" (primes are used here and hereinafter to differentiate wedge material shapes only) has at least two sides substantially parallel. A first parallel side 104 has a first ultrasonic transducer 106 mounted thereon and a second parallel side 108 immersible into said fluid whereby a first portion of an ultrasonic signal emanating from said first ultrasonic transducer 106 strikes the second parallel side 108 and reflects back to the first parallel side 104. The wedge material 102', 102" further has (a) a first non-parallel side 200, 300 from which emanates a second reflected ultrasonic signal toward a second non-parallel side 202; and (b) a receiving ultrasonic transducer 204 mounted on the second non-parallel side 202 for receiving the second reflected ultrasonic signal.

In FIG. 2, each of the first and second non-parallel sides 200,202 is connected to the first and second parallel sides 104, 108. A transmitting transducer 206 is mounted on the first non-parallel side 200 whereby the transmitting transducer transmits said second ultrasonic signal that reflects from said second parallel side 108 creating the second reflected ultrasonic signal that is received by the receiving transducer 204.

In FIG. 3, the first non-parallel side 300 is a cut in the second parallel side 108 and the second non-parallel side 202 is connected to the first and second parallel sides 104, 108, whereby an ultrasonic signal transmitted by the first transducer is reflected by both the second parallel side 108 and the first non-parallel side 300 producing a reflected signal from the second parallel side 108 to the first transducer and producing said second reflected signal from the first non-parallel side 300 to the receiving transducer 204. For the embodiments shown in FIGS. 2 and 3, it is necessary to know a-priori the speed of sound in the wedge material 102', 102" and the sign (positive or negative) of the reflection coefficient for the wedge material/fluid combination.

The angle theta of the non-parallel sides 200, 202, 300 to the second parallel side 108, equal to the angle of internal reflection, is critical to the present invention for sensitivity to small changes in fluid density. An angle of 20° provided limited sensitivity whereas an angle of about 60° provided greater sensitivity to changes in fluid density. Accordingly, the angle theta is preferable greater than about 20° and more preferable greater than about 30°.

Figure 4:
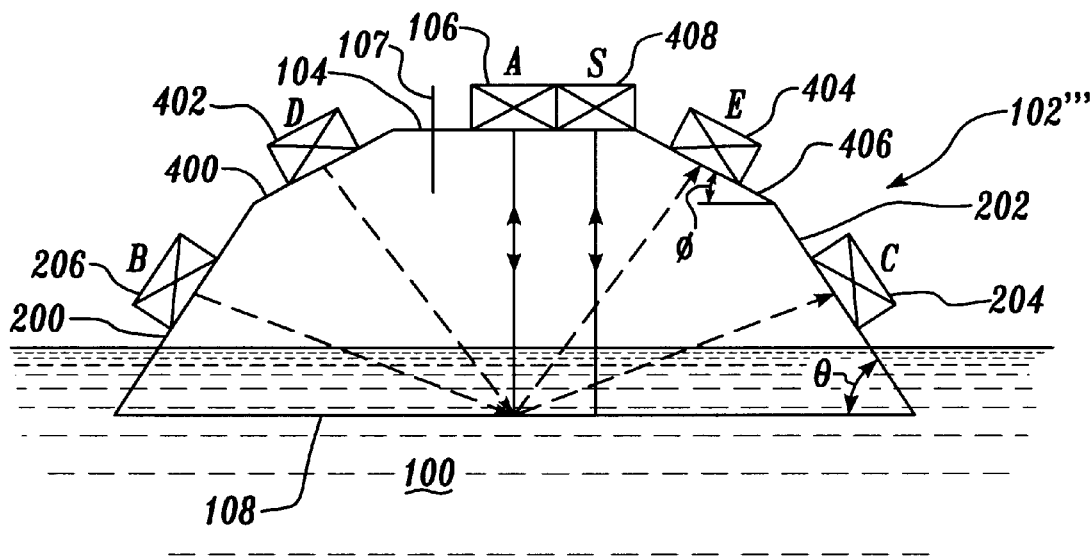
FIG. 4 is a six transducer embodiment of the present invention.

The FIG. 4 embodiment is similar to the one shown in FIG. 2 but having additional sides and transducers permitting in-situ measurement of speed of sound in the wedge material 102 and in-situ determination of the sign of the reflection coefficient. More specifically, a third non-parallel side 400 has a second transmitting ultrasonic transducer 402 that emits a third ultrasonic signal that reflects from the second parallel side 108 and creates a third reflected ultrasonic signal that is received by a second receiving ultrasonic transducer 404 mounted on a fourth non-parallel side 406. The third and fourth non-parallel sides 400, 406 make a second angle phi with said first parallel side different from the first angle theta. These additional sides and transducers are used to determine the sign of the reflection coefficients. Alternatively, analysis of signal phase may be done to determine the sign of the reflection coefficient without using the second transmitting and receiving transducers 402, 404. However, additional electronic circuitry and possibly additional software for data reduction would be needed for analysis of signal phase, which is less preferred. A fourth transmitting ultrasonic transducer 408 is mounted on the first parallel side 104 for determination of the speed of sound of the shear wave in the wedge material 102'''. The speed of sound of the longitudinal wave is measured by the pulse-echo measurement or by a pitch-catch measurement.

The transducers may be any ultrasonic transducers, preferably emitting in a range from about 0.5 MHZ to about 10 MHZ.

Electrical signals from the transducers may be collected for analysis in at least two ways. In one way, A function generator (not shown) may be applied to the transmitting transducer 206. The ultrasound reflected at the second parallel side 108 of the wedge material 102''' produces a response in the receive transducer 204. This RF-signal, after amplification (or attenuation) by a receiver (not shown) may be sent to a peak detector (not shown). After selecting a window around the RF-signal of interest, the peak detector outputs a DC-voltage that is proportional to the maximum of the RF-voltage in the window.

Alternatively, a 12-bit digitizer may be used so that extremely small changes in the voltage can be detected. When a 12-bit digitizer is used, the maximum value of the signal will be determined using software. A multiplexer system will sequentially send the toneburst signal to each send transducer and obtain the return signal. An algorithm will be developed to take averages and, in the case of the slurry, to look for minimum values in the signal and to process this data to produce an on-line value of the density and velocity of sound.

Figure 5A:
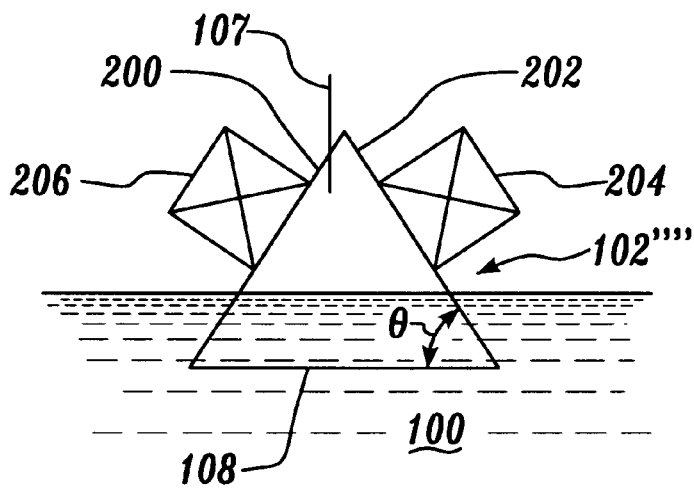
FIG. 5a is a pitch-catch block for experiments and for process control.

A preferred embodiment for a density monitor is a two-transducer wedge as shown in FIG. 5a. A temperature sensor 107, for example a thermocouple, is attached to the wedge material 102'''. In a process control application, a particular density within a defined range is known. Thus, density samples of the desired and acceptable range may be used to obtain a tabulation of transducer voltage as a function of density and temperature. The two-transducer with temperature sensor wedge may then be deployed to obtain transducer voltage measurements and wedge temperature measurements that may be used to obtain or interpolate density from the tabulation. Although this concept is similar to the measurement of the speed of sound often used for process control, in which the speed of sound and temperature are used to determine the density using a look-up table, the measurement of a voltage is a simpler procedure than the measurement of the velocity of sound thereby simplifying the process control.

EXAMPLE 1

Figure 5B:
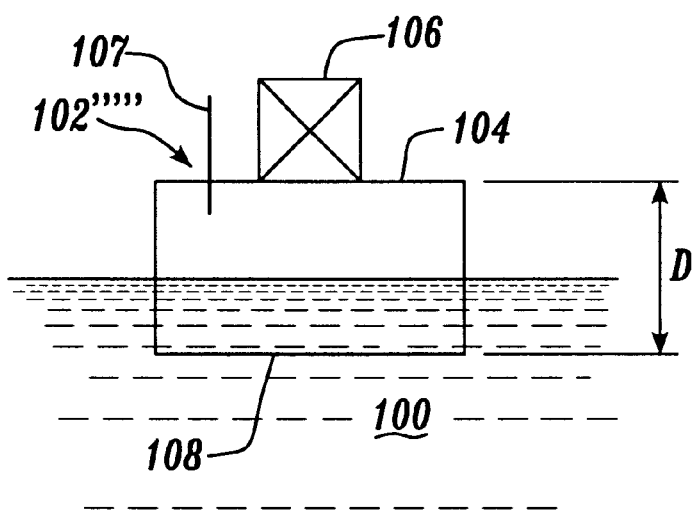
FIG. 5b is a pulse-echo block for experiments.

An experiment was conducted to demonstrate the ultrasonic densitometer of the present invention. For the experiment, two wedges were used. FIG. 5a and FIG. 5b shows the experimental setup for the pitch-catch mode, FIG. 5a, and the pulse-echo mode, FIG. 5b. The wedge material 102'''and 102'''' is Rexolite. For the pitch-catch, FIG. 5a, the wedge material is an equilateral triangular solid with an angle theta of about 60°. For the pulse-echo, FIG. 5b, the distance D between the first transducer 106 and the second parallel side 108 was 2.7 cm.

A 12-cycle toneburst at a frequency of 2.25 MHZ, produced by the Wavetek 901 function generator, was applied to the transmitting transducer 206. The ultrasound reflected at the second parallel side 108 of the wedge material 102'''' and 102''''' produced a response in the receive transducer 204. This RF-signal, after amplification (or attenuation) by an MR101 receiver, was sent to a Panametrics GPD-5052 peak detector. After passing through an RC circuit with a time constant of 10 milliseconds to minimize fluctuations, the DC voltage was measured by a DC-voltmeter to any accuracy of three decimal places.

The reflection coefficient was determined by comparing the amplitude of the RF-voltage (or toneburst) of the received signal (or echo) when the second parallel side 108 of the wedge material 102'''' and 102''''' is immersed in the liquid with that when it is air. Since the voltage of the received signal is directly proportional to the pressure and to the reflection coefficient, the following relationship is obtained:

$$Rc_{liq} = Rc_{air}(V_{liq}/V_{air})$$

where
RC is reflection coefficient, and
V is voltage from the transducer.

The reflection coefficient is a function of (1) density of the wedge material 102'''' and 102''''', (2) speed of sound of the longitudinal wave, (3) speed of sound of the shear wave, (4) the angle of incidence of the longitudinal wave with respect to the second parallel side 108, (5) the density of the fluid, and (6) the speed of sound in the fluid (See J. Krauthkramer and H. Krauthkramer, *Ultrasonic Testing of Materials*, Springer-Verlag, Third Edition, 1983, pp 606–607, Equation A.10). By obtaining measurements at two angles, pulse echo at zero degrees and pitch-catch at another angle, two equations for the reflection coefficients are provided having the unknowns of density of the fluid and speed of sound in the fluid.

The speed of sound in Table E1-1 was measured using the time-of-flight method having an uncertainty of about 2%.

The fluid used in this experiment was water with varying amounts of sugar. Samples 2–8 received increasing amounts of sugar. The sugar was commercially available cane sugar. Table E1-1 shows the density obtained by weighing fluid samples in a 50-ml volumetric flask. Table E1-1 also shows the voltage ratio data for reflection coefficients obtained using the pulse-echo block and the pitch-catch block with a 60° angle. In each case an average DC-voltmeter reading was obtained when the interface was immersed in the liquid and when in air. From this voltage ratio data, the reflection coefficients were derived.

TABLE E1-1

Parameter Standards For Water Samples

| Sample | Sugar Conc. | Density Kg/m³ | Speed of Sound (m/s) | Pitch-Catch $V_{liq}/V_{air}$ | Pulse-Echo $V_{liq}/V_{air}$ |
|---|---|---|---|---|---|
| 1 | 0.00 | 997 | 1483 | 0.3245 | 0.2477 |
| 2 | >0.00 | 1011 | 1498 | 0.3454 | 0.2380 |
| 3 | >0.00 | 1024 | 1510 | 0.3625 | 0.2287 |
| 4 | >0.00 | 1036 | 1523 | 0.3802 | 0.2193 |
| 5 | >0.00 | 1055 | 1537 | 0.4052 | 0.2066 |
| 6 | >0.00 | 1060 | 1542 | 0.4133 | 0.2016 |
| 7 | >0.00 | 1070 | 1554 | 0.4265 | 0.1942 |
| 8 | >0.00 | 1087 | 1567 | 0.4514 | 0.1805 |

The objective is to convert the pulse-echo at zero degrees and pitch-catch at 60° RF-voltage ratios to reflection coefficients, solve the inverse problem to obtain the density and velocity of sound in the liquid, and compare them with the densities and velocities of sound shown in Table E1-1.

The reflection coefficient is very sensitive to the longitudinal wave velocity and the shear wave velocity. This sensitivity has been used to determine these velocities to four significant figures. These values will be used in all further calculations: longitudinal wave velocity in Rexolite $c_L$=2337 m/s, shear wave velocity in Rexolite $c_T$=1157 m/s.

A reflection coefficient is obtained by multiplying the RF-voltage ratio by the reflection coefficient for air. The reflection coefficient for air at 0E° is −1.00 and at 60E°, +0.4170. Table E1-2 give the ultrasonically derived velocities of sound and densities of the eight liquid samples.

TABLE E1-2

Ultrasonically Derived Parameters

| Sample | Speed of Sound (m/s) | % error | Density (kg/m³) | % error |
|---|---|---|---|---|
| 1 | 1481 | −0.13% | 988.0 | 1.10% |
| 2 | 1498 | 0.00% | 1007.0 | −0.44% |
| 3 | 1503 | −0.46% | 1024.2 | −0.02% |
| 4 | 1510 | −0.85% | 1039.6 | 0.33% |
| 5 | 1522 | −0.98% | 1059.1 | 0.40% |
| 6 | 1519 | −1.50% | 1071.1 | 1.10% |
| 7 | 1522 | −2.10% | 1086.8 | 1.61% |
| 8 | 1527 | −2.66% | 1114.8 | 2.60% |

There is very good agreement between the two sets of measurements. These results show that using two reflection coefficients is a viable method for determining the density and the velocity of sound in an aqueous solution to an accuracy of at least 3%.

EXAMPLE 2

An experiment was conducted to use the present invention with non-aqueous liquids. The same apparatus as described in Example 1 were used. Results are shown in Table E2-1.

TABLE E2-1

Non-aqueous liquids

| Sample | Liquid | Density (kg/m³) | Density Error | Speed of Sound (m/s) | Sound Error |
|---|---|---|---|---|---|
| 9 | 2-propanol | 782.6 | −0.72% | 1157.3 | −1.4% |
| 10 | Paraffin Oil | 877.2 | 3.12% | 1470.6 | −6.6% |

Reasonable agreement was achieved with non-aqueous fluids.

EXAMPLE 3

An experiment was conducted to demonstrate measuring the average bulk density of an aqueous slurry with the present invention. The apparatus described in Example 1 was used.

A slurry was mixed using Potter's silicon dioxide particulate (Type 13) in water. The particulate had a maximum diameter of 0.00381 cm. For ultrasound produced by a 2.25 MHZ transducer, the wavelength in water is 0.066 cm. Since the resolution of a wave is approximately equal to its wavelength, the ultrasound should not be able to resolve individual particles in this slurry and measurements should, therefore, determine the average density and average velocity of sound.

The slurry was placed in a 2000 ml beaker and a mixer kept the slurry from settling. The slurry had a density of 1143.1 kg/m³.

Calculations of ultrasonic data were carried out for the slurry and yielded a density of 988 kg/m³, which is 13.6% low compared to the actual density. The source of the problem seemed to be that the mixer was aerating the slurry. The wedge material was re-oriented to a vertical position to minimize accumulation of air bubbles. In addition, the method of taking the measurements was altered. Instead of taking the average value of the voltmeter readings, the minimum value that repeated within a 30–60 second interval (to the second decimal place) was recorded. This reading would correspond to a minimum effect due to air and would give a truer reading of the slurry's non-aerated density.

Additional slurry samples were then subjected to the modified experimental procedure with results shown in Table E3-1.

TABLE E3-1

Slurry Sample Density Data

| Sample | Density (kg/m³) | Ultrasonic Density (kg/m³) | Percent Error |
|---|---|---|---|
| S-1 | 1143.1 | 1083.2 | −5.24% |
| S-2 | 1097.3 | 1069.9 | −2.49% |
| S-3 | 1077.0 | 1049.8 | −2.52% |
| S-4 | 1050.4 | 1051.6 | 0.11% |
| S-5 | 1037.6 | 1041.3 | 0.36% |
| S-6 | 1065.5 | 1.53.6 | −1.11% |

There is only one sample with an error at about 5%. All other samples are within 3%.

EXAMPLE 4

Using the Rexolite wedge materials as in Example 1, (FIG. 5a and FIG. 5b) and glycerine as the fluid, it was discovered that the pulse-echo signal was so weak as to be essentially non-existent. This was because the acoustic impedance of glycerine nearly matches the acoustic impedance of Rexolite ($2.5(10^6)$kg/m²s). Accordingly, a different plastic material would be used for the pulse-echo wedge material.

EXAMPLE 5

A further experiment was conducted using the embodiment shown in FIG. 4 to evaluate individual signals in measuring small changes in density. Sugar water solutions were used to test the density sensor and to determine the minimal change in density that could be observed. In the tables, the notation "SW-224" means that 224 grams of sugar were added to 1.9 kg of water, and so on, for the other four solutions. The notation "SW20%" means that the sugar content of the solution was 20% by weight, and similarly for two other solutions. The "known density" in Table E5-1 was obtained from calculations based upon the actual measured weights of sugar and water for each solution. The "measured density" in Table E5-1 was obtained with the apparatus of the present invention with dual pitch catch and dual pulse echo as indicated in FIG. 4, wherein the probe head (wedge material and transducers) was completely submerged in the sugar water solution to maintain a uniform temperature throughout the wedge.

TABLE E5-1

Density (g/cm³) of Sugar Water Solutions

| Sample | Known Density | Measured Density | Density Error (%) |
|---|---|---|---|
| SW-224 | 1.039 | 1.03 | −0.87 |
| SW-236 | 1.04 | 1.037 | −0.29 |
| SW-248 | 1.041 | 1.039 | −0.19 |

TABLE E5-1-continued

Density (g/cm³) of Sugar Water Solutions

| Sample | Known Density | Measured Density | Density Error (%) |
|---|---|---|---|
| SW-260 | 1.044 | 1.043 | −0.10 |
| SW-272 | 1.047 | 1.049 | −0.14 |
| SW10% | 1.04 | 1.038 | −0.19 |
| SW20% | 1.083 | 1.097 | +1.29 |
| SW30% | 1.129 | 1.121 | −0.71 |

Table E5-2 shows the voltage measured using the embodiment shown in FIG. 4 using transducers 402, 404 for 40° (VDE), transducers 204, 206 for 60° (VBC), and transducer 106 for 0° (VAA) for five sugar water solutions. Comparing voltage values for SW-224 and SW-272, one sees that VDE changes by 13%, while VBC and VAA change only by 3%. Thus, the voltage VDE is the most sensitive to small changes, differences or variations in the density. Twelve measurements of VDE when the probe head was immersed in sugar water SW-236 gave an average voltage of 0.225151 with a standard deviation of 0.000397. The temperature was held substantially constant at a room temperature of 20.5° C.

TABLE E5-2

Variation in voltage measurements for small changes in density

| Ident. | VBC (volts) | VDE (volts) | VAA (volts) |
|---|---|---|---|
| Water | 0.0826 | 0.2055 | 0.3318 |
| SW-224 | 0.2216 | 0.2482 | 0.2846 |
| SW-236 | 0.2258 | 0.2489 | 0.2855 |
| SW-248 | 0.2367 | 0.2519 | 0.2811 |
| SW-260 | 0.2449 | 0.2544 | 0.2798 |
| SW-272 | 0.2512 | 0.2564 | 0.2765 |

Thus, for process control, the embodiment of FIG. 5a with a temperature sensor and an angle θ of about 40° is preferred.

Closure

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

I claim:

1. An ultrasonic densitometer for process control of a density of a fluid, said ultrasonic densitometer having a wedge material, said wedge material having at least two sides substantially non-parallel, a first non-parallel side having a first ultrasonic transducer mounted thereon and a second non-parallel side immersible into said fluid whereby an ultrasonic signal emanating from said first ultrasonic transducer strikes said second non-parallel side and reflects a reflected ultrasonic signal; the improvement comprising:

said wedge material having a third non-parallel side with a second transducer for receiving the reflected ultrasonic signal, said wedge material further having an angle of internal reflection about equal to the zero reflection coefficient angle; and a temperature sensor attached to said wedge material for combining a wedge material temperature with a transducer voltage to confirm temperature uniformity of said wedge material for process control.

2. The ultrasonic densitometer as recited in claim 1 wherein the angle of internal reflection is within about 5° of the zero reflection coefficient angle.

3. The ultrasonic densitometer as recited in claim 2, wherein said angle of internal reflection is about 40°.

4. A method of process control of a density of a fluid using an ultrasonic densitometer having a wedge material, said wedge material having at least two sides substantially non-parallel, a first non-parallel side having a first ultrasonic transducer mounted thereon and a second non-parallel side immersed into said fluid, the method having the steps of:

(a) emanating a first ultrasonic signal from said first ultrasonic transducer and striking said second non-parallel side and reflecting a reflected ultrasonic signal;

the improvement comprising the steps of:

receiving the reflected ultrasonic signal with a second transducer mounted on a third non-parallel side on said wedge material; and measuring a temperature of said wedge material for combining said temperature with a transducer voltage for process control.

5. The method as recited in claim 4 wherein an angle of internal reflection in the wedge material is within about 5° of the zero reflection coefficient angle.

6. The method as recited in claim 5, wherein said angle of internal reflection is about 40°.

* * * * *